United States Patent [19]

Hughes

[11] 4,052,401
[45] Oct. 4, 1977

[54] PRODUCTION OF 3-(1',3'-DIOXANE)-PROPIONALDEHYDE COMPOUNDS

[75] Inventor: Oscar Richard Hughes, Chatham, N.J.

[73] Assignee: Celanese Corporation, New York, N.Y.

[21] Appl. No.: 720,788

[22] Filed: Sept. 7, 1976

Related U.S. Application Data

[62] Division of Ser. No. 640,618, Dec. 15, 1975, Pat. No. 4,003,918.

[51] Int. Cl.$^2$ .................................... C07D 319/04
[52] U.S. Cl. .................................................. 260/340.7
[58] Field of Search ...................................... 260/340.7

[56] References Cited

U.S. PATENT DOCUMENTS 3,929,915   12/1975   Cumbo et al. ............ 260/340.7 X

FOREIGN PATENT DOCUMENTS 2,334,378   1/1975   Germany ................ 260/340.7

Primary Examiner—Ethel G. Love

[57] ABSTRACT

This invention provides a process for producing 2-vinyl-1,3-dioxane compounds rapidly and efficiently by contact of a mixture of acrolein and a 1,3-propanediol compound with solid cation exchange resin in acid form. There is further provided a process for conversion of acrolein into 3-(1',3'-dioxane)propionaldehyde derivatives.

2 Claims, No Drawings

PRODUCTION OF 3-(1',3'-DIOXANE)-PROPIONALDEHYDE COMPOUNDS

This is a division of application Ser. No. 640,618, filed Dec. 15, 1975, now U.S. Pat. No. 4,003,918.

BACKGROUND OF THE INVENTION

The synthesis of acyclic and cyclic acetals are described in the chemical literature, and in patent literature such as U.S. Pat. Nos. 2,678,950; 2,888,492; 2,915,530; 2,987,524; 3,014,924; and the references cited therein.

Conventional processes for the direct condensation of alpha, beta-unsaturated aldehydes and polyols in the presence of acid catalysts yield large portions of impurities, principally beta-alkoxyacetals and beta-alkoxyaldehydes which are formed by the addition of the polyols across the alpha, beta-double bond of the aldehydes. As a consequence of these undesirable side reactions, attempts have been made to prevent the formation of the aforementioned impurities by reducing the temperature and catalyst concentration; however, these modifications lead to impractically low rates of reaction.

To overcome the disadvantages of conventional processes, U.S. Pat. No. 3,014,924 proposes reacting an alpha, beta-unsaturated aldehyde with an aliphatic polyol bearing at least two hydroxyl groups bonded to different atoms in the polyol molecule in the presence of a catalyst comprising a highly-porous solid carrier having a surface area of at least 75 square meters per gram and about from 0.025 to 1.0 millimole per unit weight of carrier of a strong mineral acid.

Preferably, polyol and catalyst are added to a suitable reaction vessel together with a water-immiscible solvent which forms an azeotrope with water and the aldehyde. Next, the alpha, beta-unsaturated aldehyde is added slowly to the reaction mixture. During the reaction, water, unreacted aldehyde and azeotroping agent are continuously distilled, the water is separated, then the agent and the aldehyde are returned to the reaction vessel. Preferably the azeotroping agent is at least partially miscible with both reactants. Such preferred agents are, for example, xylene, toluene, benzene, cyclohexane, chloroform, diisobutylene, and hexane.

U.S. Pat. No. 2,888,492 describes a process for producing cyclic acetals which involves reacting an acrolein type aldehyde with a polyol in the presence of 0.02 to 0.06 mole percent based on the amount of ethylenic aldehyde present of a sulfo acid such as sulfuric acid, p-toluene sulfonic acid, ethanesulfonic acid, and the like. The reaction is carried out by heating a mixture of the chosen alpha, beta-ethylenic aldehyde and polyol, preferably containing about 5 to 50% excess of aldehyde over the stoichiometric requirement for the reaction, dissolved, or suspended in a suitable liquid such as, for instance, benzene, dichloroethylene, and the like. By refluxing at about 50° C to 90° C under a phase-separating head until the theoretical amount of water is removed, the reaction is comleted in about 1 to 3 hours, and moderate yields of unsaturated cyclic acetals are obtained.

As it is apparent from consideration of the above described processes, there remains a need for a process for direct condensation of alpha, beta-unsaturated aldehydes and polyols which is rapid and efficient and amenable to plant-scale operation.

Accordingly, it is an object of the present invention to provide an improved process for condensation of alpha, beta-unsaturated aldehydes and polyols to form acetals.

It is another object of this invention to provide a continuous process for converting acrolein into 2-vinyl-1,3-dioxane compounds.

It is a further object of the present invention to provide a commercially feasible process for converting acrolein into 3-(1',3'-dioxane)propionaldehyde derivatives.

Other objects and advantages shall become apparent from the accompanying description and examples.

DESCRIPTION OF THE INVENTION

One or more objects of the present invention are accomplished by the provision of a process for producing 2-vinyl-1,3-dioxane compounds corresponding to the formula:

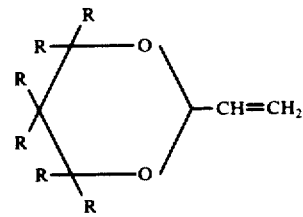

which process comprises (1) forming a liquid mixture of acrolein and diol compound of the formula:

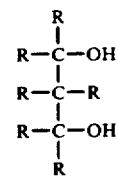

wherein R is hydrogen or an alkyl group containing between one and about five carbon atoms, and (2) contacting the acrolein-diol liquid mixture with solid cation exchange resin in acid form at a reaction temperature in the range between about −20° C and 100° C for a reaction period sufficient to achieve an equilibrium condensation between acrolein and diol compound.

In the present invention 2-vinyl-1,3-dioxane compounds corresponding to the formula represented above, and hydroformylation derivatives thereof, the vinyl or propionaldehyde substituent is attached to the 2-position of the 1,3-dioxane structure, i.e., an "acetal" configuration.

By the expression liquid hourly space velocity (LHSV) as employed herein is meant the volume of acrolein-diol feed mixture passed through a fixed bed of cation exchange resin per hour relative to the space volume of the cation exchange resin functioning as a catalyst in the invention condensation process.

The invention process is conducted for a sufficient period of time to permit the condensation reaction between acrolein and diol compound to reach a state of reaction equilibrium at a given temperature. The state of condensation equilibrium is mainly determined by the nature of the diol compound being condensed with acrolein, the molar proportions of the two reactants, and by the temperature at which the condensation reaction equilibrium is achieved.

Generally, higher temperatures favor a faster rate of condensation, and concomitantly a lower equilibrium conversion of acrolein to 2-vinyl-1,3-dioxane compound. Lower temperatures favor a slower rate of condensation but higher conversion to acetal at equilibrium.

The rate of condensation is also affected by the chemical reactivity of the diol compound under the reaction conditions. 1,3-Butanediol condenses more rapidly with acrolein than does 2-methylpropanediol, and the latter diol compound condenses more rapidly with acrolein than does 1,3-propanediol.

The reaction temperature of the present invention condensation process can vary in the range between about $-20°$ C and $100°$ C, and preferably in the range between about $-10°$ C and $75°$ C. For the condensation of acrolein with diol compounds such as 1,3-propanediol, 2-methyl-1,3-propanediol and 1,3-butanediol, the preferred condensation reaction temperature is in the range between about $10°$ C and $60°$ C. More preferably, the present invention condensation reaction is conducted at ambient temperature in the manner described in the Examples.

The molar ratio of 1,3-propanediol compound to acrolein in the invention process feed mixture can vary in the range between about 0.05:1 to 100:1, and more preferably in the range between about 0.5:1 to 10:1, moles of diol compound per mole of acrolein.

The condensation reaction time of the process is variable for the reasons set forth hereinabove. The optimal reaction time must be determined as a coordinate with the other reaction conditions being considered. In a typical batch-type process at ambient temperature, the reaction time will vary in the range between about 5 minutes and 2 hours.

The use of solid cation exchange resins as acid catalysts is particularly advantageous in the practice of the present invention process. Optimal yields of 2-vinyl-1,3-dioxane compounds are obtained with ease and efficiency. Cation exchange resins in acid form which are suitable as catalysts are commercially available with well characterized shapes, sizes, surface areas, pore sizes, exchange capcities, moisture content, acid strength, and the like. The technology of solid cation exchange resin acids is reviewed by R. M. Wheaton and A. H. Seamster in the Kirk-Othmer Encyclopeida of Chemical Technology, 2nd Ed., Vol. II, pp. 871–899.

For the purposes of the present invention process, strong acid cation exchange resins are highly preferred. These are generally copolymers of polystyrene-divinylbenzene which have benzenesulfonate groups as acid sites. Neutralization of the acid sites transforms the free acid structure into a salt. Commercial cation exchange resins are supplied both in the form of free acids and salts. Illustrative of commercial strong acid cation exchange resins are Rexyn 101 (H+) from Fischer Scientific; Dowex 50 W and Dowex MSC-1 from Dow Chemical; Amberlite 200, 200C and 252 from Rohm and Haas; Ionac C-244, C-249, C-252 and CFP-105(H+) from Ionac Chemical; and the like.

These cation exchange resins have relatively high moisture content (40–60 weight percent) and high cation exchange capacities, i.e., 1–2 meq./gram(wet) and 4–5 meq./gram(dry). It has been found that even with relatively high moisture contents these cation exchange resins are amenable for application in non-aqueous media or in organic solutions containing low concentrations of water, such as are encountered in the practice of the present invention process.

Particularly useful in the present invention process are commercial strong acid cation exchange resins adapted for non-aqueous catalyst applications. Illustrative of such cation exchange resins are Amberlyst 15, Amberlyst XN 1005 and Amberlyst SN 1010 which are supplied by Rohm and Haas. These special cation exchange resins have a moisture content less than about 3 percent.

Weakly acidic cation exchange resins are also commercially available. Characteristically these resins have carboxylate functionality rather than sulfonate functionality. Typical commercial products are Amberlite IRC-84, IRC-50, IRC-72 and DP-1 (Rohm and Haas). Employing a weakly acidic cation exchange resin catalyst in the present invention process necessitates a longer reaction time to achieve the optimum acrolein/1,3-propanediol condensation equilibrium under given reaction conditions.

During the development stage of the present invention process, it was found that an unusually high rate of conversion of acrolein to vinyl-1,3-dioxane product could be achieved by employing perfluoro sulfonic acid resin as a catalyst. For example, a feed stream of acrolein/1,3-propanediol passing through a fixed bed of Nafion 501 powder (DuPont) at ambient temperature and a LHSV of 12 yields 16 moles of acetal per liter per hour.

The acid catalyst activity tends to decline after long term use in a fixed bed, or in a slurry bed reaction medium where the feed is introduced continuously and the product mixture is withdrawn continuously. Spent acid cation exchange resins are readily reactivated by treatment with an acid solution. As an illustration, Ionac CFP 105 is fed a 24 weight percent acrolein in 1,3-butanediol solution at a LHSV of 3.8 at ambient temperature. The process is continued until there is a substantial decline in catalyst activity. The catalyst activity is then regenerated by pumping a 7 percent aqueous hydrochloric acid and 1,3-butanediol admixture through the catalyst bed. After extensive washing of the catalyst with aqueous 1,3-butanediol, the catalyst exhibits high activity for conversion of acrolein to 2-vinyl-1,3-dioxane compounds.

In a batch-type process in accordance with the present invention, the acid cation exchange resin is employed in a quantity at least sufficient to catalyze the acrolein/1,3-propanediol condensation reaction to produce an acceptable yield of 2-vinyl-1,3-dioxane product. The quantity of acid cation exchange resin employed as a catalyst can vary over a broad range between about 0.1 and 20 weight percent, based on the weight of acrolein in the reaction mixture.

In an important embodiment of the present invention process, the acid cation exchange resin is charged to a fixed bed reactor, and at ambient temperature and pressure a feed stream of acrolein and a 1,3-propanediol compound is passed through the fixed bed of resin catalyst.

The liquid hourly space velocity of the feed stream can vary over a range between about 0.1 and 50, depending on the particular 1,3-propanediol derivative employed, the molar ratio of reactants, the type of catalyst in the fixed bed, the temperature of the reaction medium, and other such considerations. When 1,3-butanediol is the diol reactant, the LHSV is preferably about 1–20, and most preferably about 10–15. In the case of 2-methyl-1,3-propanediol, the preferred LHSV range is about 0.25-20, and most preferably about 0.8-2. The preferred LHSV range when 1,3-propanediol is the diol reactant is about 0.1-20, and most preferably about 0.5-1.5 at a reaction temperature of about 25° C.

The advantages of the present invention process over the prior art derive from certain unexpected chemical and thermodynamic phenomena. As it has been demonstrated herein, acrolein can be condensed with a 1,3-propanediol compound at a high rate of conversion and in an unusually high yield in the presence of an acid catalyst at a relatively low temperature (e.g., 25° C or below). Further, the condensation is accomplished with ease and efficiency without the continuous removal of water of condensation as taught by the prior art. Most commonly, the prior art processes for converting aldehydes into acetals involve the incorporation of an azeotroping agent to remove water continuously at reflux temperature.

Hence, the present invention process achieves a high yield of 2-vinyl-1,3-dioxane products without the use of an azeotroping agent and, preferably, without the application of heat.

Another advantage of the present invention process relates to the use of strong acid cation exchange resins as catalysts. In both slurry bed and fixed bed reaction systems, the heterogeneous catalyst phase remains separate from the resultant product phase. No neutralization of acid catalyst is required, and the heterogeneous catalyst phase is undiminished and reusable.

A still further advantage of the present invention process derives from the fact that the resultant product mixture of 2-vinyl-1,3-dioxane compound and 1,3-propanediol compound and water directly can be subjected to hydroformylation conditions to yield 3-(1',3'-dioxane)propionaldehyde as a valuable product. The presence of water in the feed mixture is not deleterious, and the presence of 1,3-propanediol compound is advantageous since it performs as a solvent medium in the hydroformylation process. The amenability of the present invention product mixture to hydroformylation conditions has important commercial ramifications for the multi-stage conversion of acrolein to 1,4-butanediol via the hydrogenation of 3-(1',3'-dioxane)propionaldehyde route.

The reaction of the present invention 2-vinyl-1,3-dioxane/1,3-propanediol product mixture with hydrogen and carbon monoxide under hydroformylation conditions is conducted in the presence of a hydroformylation catalyst.

The preparation of aldehydes and alcohols by the reaction of an olefin with hydrogen and carbon monoxide in the presence of a catalyst is well known in the art, i.e., the "oxo" or "Roelen" reaction. The reaction of an olefin with carbon monoxide and water employing cobalt carbonyl, nickel carbonyl or iron carbonyl is known to produce carboxylic acids (see U.S. Pat. No. 2,448,368 and U.S. Pat. No. 2,593,440). The reaction of an olefin with carbon monoxide and water produces alcohols when conducted in the presence of an iron carbonyl-tertiary amine complex catalyst [Reppe synethesis; Liebig's Ann. Chem., 582, 133(1953)].

Cobalt catalysts for hydroformylation of olefins to produce alcohols and aldehydes are described in Kirk-Othmer, Encyclopedia of Chemical Technology, 14, 373, 2nd Ed. Cobalt catalysts are also reviewed in "Catalysis Reviews", 6 85-131 (1972), published by M. Dekker Inc.

It has been found that superior results are achieved if the hydroformylation reaction is conducted in the presence of a catalyst which is a complex of a Group VIII metal and a ligand containing phosphorus, arsenic and/or antimony elements. Tertiary amines can also be employed as a ligand in the catalyst complex.

Catalysts which are suitable for the purposes of the present invention hydroformylation process are illustrated by those described in U.S. Pat. Nos. 3,168,553; 3,239,556; 3,239,570; 3,290,379; 3,369,050; 3,420,898; 3,488,296; 3,527,818; 3,725,534; 3,816,337; 3,821,311; 3,825,601; 3,847,997; 3,857,900; 3,859,369; and the like.

Further, any of the metal-phosphine complexes disclosed in "Carbon Monoxide in Organic Synthesis", Falbe, (Springer-Verlag 1970), pages 14-25, may be used. The preferred catalysts are phosphine complexes of rhodium, cobalt, iridium and ruthenium. The most preferred catalysts have the formula $RhCOH(Q_3P)_3$, $RhCOH[(QO)_3P]_3$, $RhCOCl[(QO)_3P]_2$ and $RhCOCl(Q_3P)_2$ wherein Q is phenyl; alkyl phenyl such as tolyl, xylyl, and the like; cyclohexyl; alkyl substituted cyclohexyl such as methyl, propyl, octyl, and the like; substituted cyclohexyl; and aliphatic radical such as methyl, butyl, octyl, and the like, or mixtures of any of the foregoing. Rhodium catalysts containing tertiary amines are also important hydroformylation catalysts, e.g., a catalyst complex of rhodium metal, carbon monoxide and a trialkyl amine, triaryl amine or trialkylaryl amine.

It is worthy of note that an exceptionally high yield of straight chain 3-(1',3'-dioxane)propionaldehyde is obtained when the hydroformylation catalyst employed is a complex of rhodium metal, carbon monoxide and triarly phosphine. Illustrative of this class of catalysts is

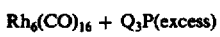

$$Rh_6(CO)_{16} + Q_3P(excess)$$

It is also to be noted that "straight chain selectivity" of product yield is promoted when the molar ratio of triaryl phophine ligand to rhodium metal in the hydroformylation reaction medium is at least 10 to 1, and as high as 400 to 1. Hence, a higher yield of straight chain 3-(1',3'-dioxane)-propionaldehyde is obtained at the expense of branched chain 2-(1',3'-dioxane)propionaldehyde.

One method for producing a 3-(1',3'-dioxane)-propionaldehyde in high yield selectivity of at least 70 weight percent comprises reacting a 2-vinyl-1',3'-dioxane compound with hydrogen and carbon monoxide in the presence of a hydroformylation catalyst as described hereinabove at a temperature between about 25° C and 200° C and a pressure between about 15 and 3000 psi.

Illustrative of a preferred embodiment, 3-(5'-methyl-1',3'-dioxane)propionaldehyde is produced in a yield of at least 80 weight percent by reacting 2-vinyl-5-methyl-1,3-dioxane with hydrogen and carbon monoxide in the presence of a metal-ligand complex hydroformylation catalyst at a temperature between 80° C and 120° C and a pressure between about 75 and 150 psi. The relative amounts of hydrogen and carbon monoxide employed can vary in accordance with conventional hydroformylation processes, i.e., a molar ration between 10:1 and 1:10. It has been observed that a high yield of 3-(5'-methyl-1',3'-dioxane)propionaldehyde is favored by increasing the relative ratio of hydrogen to carbon monoxide. Hence, to achieve the conversion of 2-vinyl-5-methyl-1,3-dioxane to 3-(5'-methyl-1',3'-dioxane)propionaldehyde in a yield of 85 weight percent and higher, a molar ratio of 1:1 to 5:1 of hydrogen to carbon monoxide is employed in the presence of hydroformylation catalyst which is a complex of a Group VIII metal and a ligand containing phosphorus, arsenic and/or antimony elements.

The hydroformylation catalyst is generally employed in a quantity between about 0.001 and 5 weight percent, based on the weight of 2-vinyl-1,3-dioxane starting material, and preferably a weight percent quantity between about 0.01 and 1.0, exclusive of the weight of ligand if present.

The following Exmples are further illustrative of the present invention. The reactants and other specific ingredients are presented as being typical, and various modifications can be devised in view of the foregoing disclosure within the scope of the invention.

EXAMPLE I

Conversion Of Acrolein To 2-Vinyl-4-methyl-1,3-dioxane

An acrolein/1,3-butanediol solution (1:2 molar ratio) having a composition on a weight basis of 19% acrolein, 77% 1,3-butanediol, 2% water and 0.4% acetal was pumped at a liquid hourly space velocity of 12 V/V hours through a tubular reactor at ambient temperature. The reactor contained a solid cation exchange resin in acid form (Rexyn 101 H, Fischer Scientific) which had been sieved to 16–20 mesh.

A clear colorless product solution was produced which had a composition on a weight basis of 49% 2-vinyl-4-methyl-1,3-dioxane, 43% 1,3-butanediol, 1.6% acrolein and 11% water.

The acrolein conversion was 93%, and the rate of acetal formation was 45 moles acetal/liter of reaction volume per hour which corresponded to 5670 grams of acetal product per hour.

EXAMPLE II

Hydroformylation Of 2-Vinyl-4-methyl-1,3-dioxane To 3-(4'-methyl-1',3'-dioxane)propionaldehyde The product solution of Example I was subjected to vacuum distillation to remove all traces of residual acrolein.

A portion of the remaining product solution of 2-vinyl-4-methyl-1,3-dioxane (99.4 grams) was charged to a 300 ml stirred "magnedrive" autoclave, along with triphenyl phosphine (30 grams) and hexarhodium hexadecacarbonyl, $Rh_6(CO)_{16}$ (0.1 gram).

The reactor was heated to 73° C under one atmosphere of carbon monoxide, then to a constant pressure of 90 psig with a 1:1 mixture of carbon monoxide and hydrogen. The temperature increased slowly to 86° C over a period of about 100 minutes.

The reactor was cooled to room temperature, and the product mixture was recovered (130.8 grams). Gas chromatography indicated that all of the acrolein was converted into a mixture of 3-(4'-methyl-1',3'-dioxane)propionaldehyde and 2-(4'-methyl-1',3'-dioxane)propionaldehyde.

The reaction mixture was distilled at about 7.8–10 mm Hg pressure and a temperature of 90°–102° C to yield an aldehyde fraction and a 1,3-butanediol fraction.

A portion of the aldehyde fraction (20 grams), water (30 grams) and Raney nickel (0.5 gram) were charged into the autoclave and heated to 198° C under 400–435 psig of hydrogen. Total reaction time was 120 minutes.

The product mixture was cooled and analyzed by gas chromatography. The aldehyde starting material had converted completely into a mixture of 1,3-butanediol and 1,4-butanediol.

EXAMPLE III

Production Of 2-Vinyl-5-methyl-1,3-dioxane

An acrolein/2-methylpropanediol solution (1:2 molar ratio) having a composition on a weight basis of 27% acrolein, 71% 2-methyl-1,3-propanediol, 1.8% water and 0.4% acetal was pumped through a tubular reactor at a space velocity of 0.8 V/V hour at ambient temperature. The reactor contained a fixed bed of Rexyn 101 H.

A product mixture was obtained which on a weight basis consisted of 55% 2-vinyl-5-methyl-1,3-dioxane, 36% 2-methyl-1,3-propanediol, 2% acrolein and 8% water.

Acrolein conversion was 92%, and the rate of acetal formation was 3.4 moles acetal/liter hour.

EXAMPLE IV

Production Of 2-Vinyl-1,3-dioxane

An acrolein/1,3-propanediol solution (1:2 molar ratio) having a composition on a weight basis of 20% acrolein, 74% 1,3-propanediol, 2.8% water and 2.9% acetal was pumped at 1.1 LHSV through a tubular reactor containing Rexyn 101 H (16–20 mesh) at room temperature.

The resulting product mixture had a composition by weight of 46% 2-vinyl-1,3-dioxane, 42% 1,3-propanediol, 3.5% acrolein and 9% water.

Acrolein conversion was 82%, and the rate of acetal formation was 4.1 moles acetal/liter hour.

EXAMPLE V

Process Improvement With Perfluoro Sulfonic Acid Catalyst

A quantity of Nafion 501 (K+) perfluoro sulfonic acid ion exchange resin powder (DuPont) was swelled in boiling water for 30 minutes and then treated several times with 15% nitric acid to convert the ion exchange resin into the acid form. The acidified resin was washed with distilled water until the washings were neutral. The resin was then contacted with 1,3-butanediol and allowed to swell overnight at a temperature of 50°–100° C.

The reactor of the previous Examples was loaded with the prepared acidified resin. In the manner of Example IV, an acrolein/1,3-propanediol solution was pumped through the reactor at a LHSV of 3.9.

The resulting product mixture had a lower by-product concentration than in Example IV. Acrolein conversion was the same (82%) but the acetal formation rate was substantially higher i.e., 16 moles acetal/liter hour.

EXAMPLE VI

Production Of 2-Vinyl-1,3-dioxane By a Batch Process

Acrolein (4.3 ml) and 1,3-propanediol (10 grams) were mixed and stirred at room temperature for several hours. Analysis indicated that no reaction or decomposition occurred.

To the stirring mixture there was then added 0.051 gram of Ionac CFP-105(H+) from Ionac Chemical Co. This catalyst is a macroporous strong acid ion exchange resin with less than 5% moisture content.

The formation of acetal product commenced immediately upon the addition of the acid catalyst. During the first 30 minutes of reaction time the formation of 2-vinyl-1,3-dioxane was at the rate of about 18 moles per liter of liquid volume per hour. After 93 minutes, a 61% conversion of acrolein had occurred. The selectivity to acetal product was in the range of 95–100%.

When the reaction mixture containing the acid catalyst was permitted to stand for several days, there was an accumulation of by-products, and the selectivity to acetal product declined to 83%.

EXAMPLE VII

Effect Of Process Temperature On Acetal Yield

Acrolein (8.6 ml), 1,3-propanediol (20 grams) and 0.1 gram Ionac CFP-105(H+) were mixed and stirred together at room temperature for several hours to achieve an equilibrium mixture of acrolein, 1,3-propanediol, 2-vinyl-1,3-dioxane, and water. The catalyst was removed by filtration, and the product solution was divided into part A and part B.

To part A there was added 0.05 gram of Ionac CFP-105, and then both part A and part B solutions were stirred at 80° C. Periodically samples from each solution were analyzed by gas chromatography.

In the original undivided product solution (i.e., the room temperature reaction mixture) the 2-vinyl-1,3-dioxane product was produced with a by-product inefficiency of 7% by weight.

The acetal yield in part A decreased rapidly upon heating at 80° C. After 300 minutes of heating time, the by-product yield in part A had increased to about 40%. Under the same conditions of temperature and time, the part B solution was stable, and the final yield of by-product was only 8%.

This Example demonstrates that by-products form rapidly if an acrolein/diol/acetal/water mixture is heated in the presence of acid catalyst, but that it is relatively stable in the absence of acid catalyst. The by-product formation that occurs on heating the reaction mixture is similar to that which forms during azeotrope separation (e.g., at 80° C with benzene as the azeotroping agent) or distillation at the same elevated temperatures.

Hence, it is an advantage of the present invention process that acrolein can be condensed with a 1,3-propanediol to form a 2-vinyl-1,3-dioxane compound in the presence of a solid acid catalyst without heating, and the product can be separated from the acid catalyst and recovered without heating.

What is claimed is:

1. A process for producing 3-(1',3'-dioxane)-propionaldehyde compounds which comprises (1) forming a liquid feed mixture of acrolein and a diol compound of the formula:

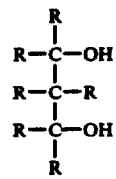

wherein R is hydrogen or methyl; (2) passing the acrolein-diol feed mixture through a fixed bed of perfluoro sulfonic acid cation exchange resin in acid form, at a liquid hourly space velocity between about 0.1 and 50 and a reaction temperature in the range between about 10° C and 60° C, to yield an effluent mixture containing 2-vinyl-1,3-dioxane product; and (3) subjecting the effluent mixture to hydroformylation conditions to produce 3-(1'3'-dioxane)propionaldehyde corresponding to the formula:

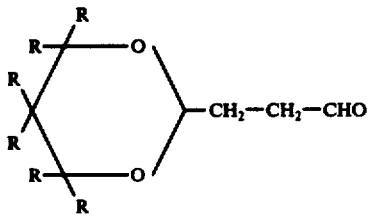

wherein R is hydrogen or methyl.

2. A process in accordance with claim 1 wherein the effluent mixture is freed of acrolein before being subjected to hydroformylation conditions.

* * * * *